United States Patent [19]
Iwamoto et al.

[11] 4,103,162
[45] Jul. 25, 1978

[54] APPARATUS FOR THE CONTINUOUS MEASUREMENT OF THE CONCENTRATION OF OIL

[75] Inventors: Michinori Iwamoto; Toshiyuki Nomura, both of Kyoto

[73] Assignee: Horiba, Ltd., Kyoto, Japan

[21] Appl. No.: 749,618

[22] Filed: Dec. 10, 1976

[30] Foreign Application Priority Data

Jan. 12, 1976 [JP] Japan ................................. 51-2642

[51] Int. Cl.² .......................................... G01N 21/34
[52] U.S. Cl. ..................................... 250/343; 250/301
[58] Field of Search ............... 250/301, 343, 344, 345, 250/346

[56] References Cited
U.S. PATENT DOCUMENTS

| | | |
|---|---|---|
| 2,765,409 | 10/1956 | Hutchins et al. ..................... 250/343 |
| 2,883,343 | 4/1959 | Favre et al. ..................... 250/345 X |
| 3,462,596 | 8/1969 | Saunders ........................... 250/343 X |
| 3,917,945 | 11/1975 | Sema et al. ............................ 250/301 |

*Primary Examiner*—Archie R. Borchelt
*Attorney, Agent, or Firm*—Wenderoth, Lind & Ponack

[57] ABSTRACT

The present invention relates to an apparatus for continuously measuring the concentration of oil in a water sample by the infra-red absorption method. The apparatus comprises a supplying device which supplies an oil-containing water sample and a supplying device which supplies a solvent for extracting the oil in the sample, each of said water sample and solvent being supplied in a controlled and continuous amount, an extractor connected to said supplying device having an agitator therein, which extractor receives said oil-containing water sample and solvent and serves to extract the oil component in the water sample with the solvent.

3 Claims, 3 Drawing Figures

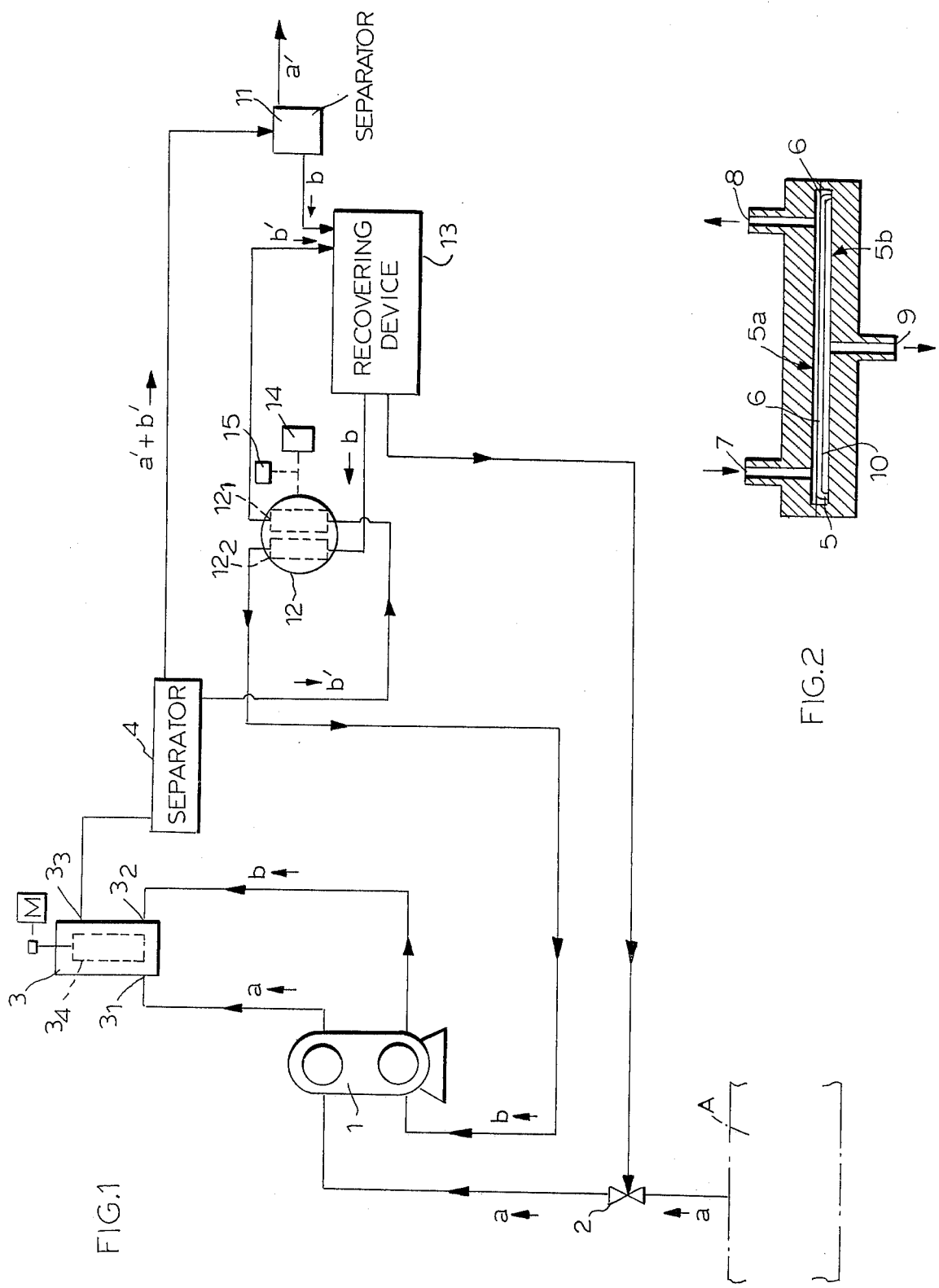

APPARATUS FOR THE CONTINUOUS MEASUREMENT OF THE CONCENTRATION OF OIL

FIELD OF THE INVENTION

The present invention relates to an apparatus for continuous measurement of the concentration of oil.

DESCRIPTION OF THE PRIOR ART

As methods for the measurement of the concentration of oil, there may be exemplified the following methods:

(1) A gravimetric analysis of the oil content to determine the oil content from the change of weight by utilizing an extraction technique with n-hexane.

(2) A turbidmetric method to determine the oil content by the measurement of the light intensity of scattered light by irradiating a solution containing droplets of oil in a state of dispersion.

(3) A fluorescence photometric method to determine the oil content in a sample solution by the measurement of the light intensity of fluorescence emitted from the sample solution by the irradiation of the oil-containing sample solution with an ultra-violet ray of a definite wave length.

(4) A method of determining the oil content by the measurement of light absorption of the ultra-violet ray irradiated into a sample solution containing oil in the above example (3).

(5) An infra-red absorption method to determine the amount of oil contained in a solvent used for the extraction of oil by the observation of the light absorption of an infra-red ray irradiated onto the oil-containing solvent.

Among these methods, the infra-red absorption method is considered to be superior, since the sensitivity is very high if the method is compared with other methods exemplified above and the change of sensitivity due to the differences in the kinds of oils examined is rather small.

The present invention relates to an apparatus for the continuous measurement of the concentration of the oil content, depending upon the infra-red absorption technique mentioned above.

As stated above, though the sensitivity of the infra-red absorption method is surely very superior to the sensitivities of other analytical methods, this method also has serious disadvantages. That is, since the existence of water introduces an error in the measurement, it is necessary to carry out an extraction with an organic solvent and to separate the thus-obtained solution. This has forced the art-skilled to design apparatus used for the measurement of the oil content in such a manner as to be employed in a batch system or in a semi-continuous system, depending upon the infra-red absorption technique. However, no apparatus has yet been designed in which the infra-red absorption technique could be operated in a completely continuous manner. On top of this disadvantage, the previous methods utilizing this technique have suffered from the disadvantages that the response in the measuring operation is slow. Moreover, another disadvantage of the infra-red absorption method is that the accuracy of this method decreases as the capacity of the adsorbent used for recovering the solvent from the extracted solution in a recovery device decreases.

SUMMARY OF THE INVENTION

The present invention provides an apparatus which makes it possible to carry out a completely continuous measurement of the oil concentration using the infra-red absorption technique. Further, according to the present invention, the measuring response of the apparatus is rapid as opposed to previous devices and the accuracy of the apparatus in measuring the oil content is sufficiently accurate, even though the ability of the absorbent to recover the solvent decreases as mentioned above. Thus, the present invention overcomes the classical disadvantages of the conventional infra-red absorption oil measuring devices previously discussed.

BRIEF DESCRIPTION OF THE DRAWINGS

The attached drawings show one way to practice the present invention. In the drawings, FIG. 1 is a flow sheet showing the whole system of an apparatus used to practice the present invention.

FIG. 2 is a vertical sectional view of the first separator and

DETAILED DESCRIPTION OF THE PREFERRED EMBODIMENTS

Figure 3:
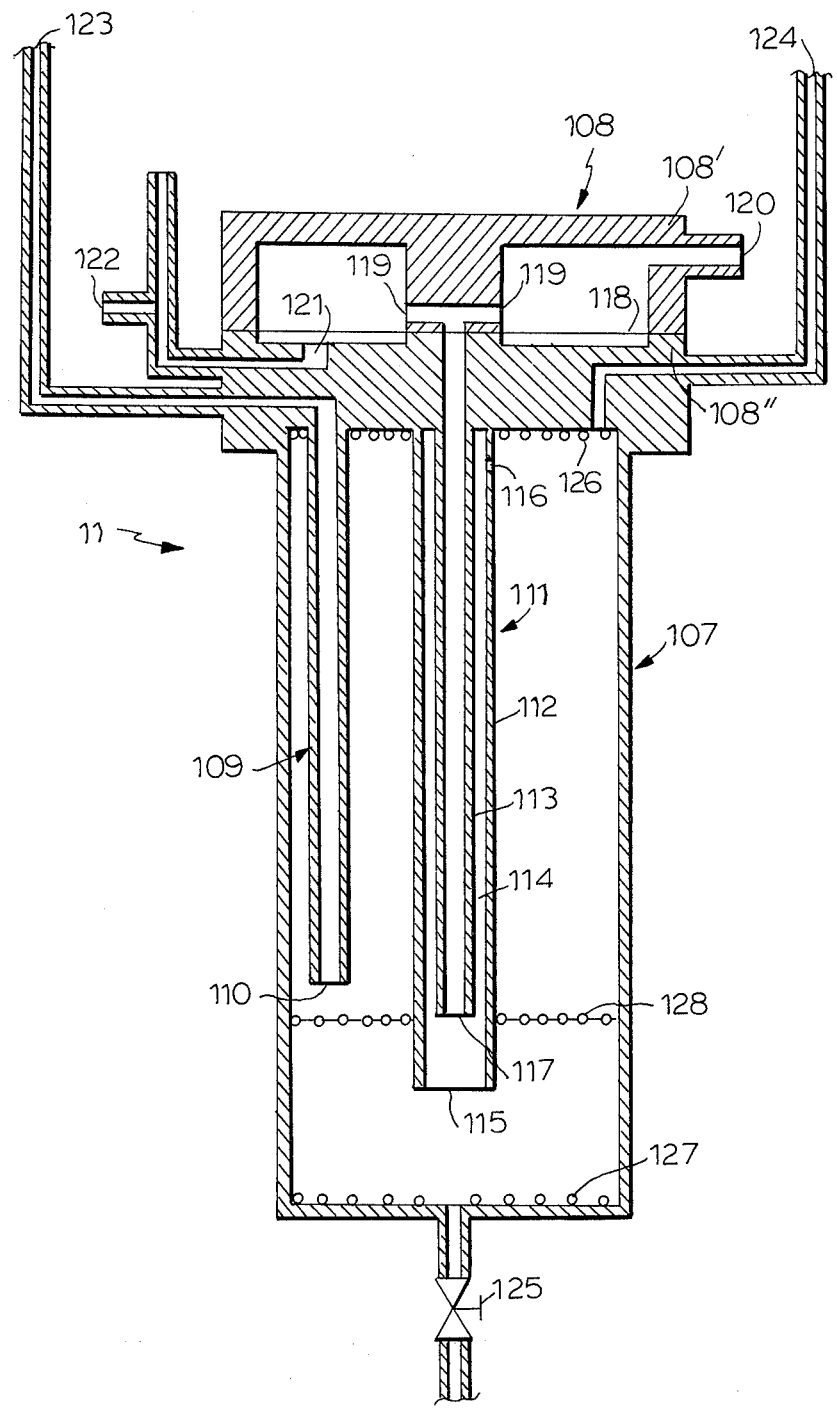
FIG. 3 is a vertical sectional view of the second separator.

The present invention will now be explained in detail with reference to the attached drawings.

FIG. 1 shows the construction of an apparatus of the present invention used for a continuous measurement of the oil concentration in a water sample. In FIG. 1, 1 is a metering pump which is controlled to pump a definite amount of a sample water (for example, a waste water in a channel A from a factory) through a magnetic valve 2 and at the same time, controlled to pump a definite amount of a solvent b (for example, carbon tetrachloride or fluorocarbon solvent (e.g. Freon 113 of E. I. Du Pont Corportion)) from the other channel. An extractor 3 with an agitator is used to extract the oil contained in the sample water a with the solvent b continuously supplied to the extractor through the pump 1, by mixing them effectively under agitation. $3_1$ and $3_2$ are inlets, $3_3$ is an outlet and $3_4$ shows agitator plates which are continuously driven by a motor M. 4 is the first separator which separates the mixture of liquids, sent from the extractor 3, into two components, that is, component b' which is a solution consisting of the organic solvent and the oil contained in the sample solution a and component a' which is the remainder of the sample water left after the removal of the oil by extraction.

Since it is desirable that the separator 4 have an ability to separate the mixture of two liquids into the two components as soon as possible (in order to shorten the time lag from the sampling of the sample water to the analysis), it has a structure as shown in FIG. 2, wherein the principal of the separation is to carry it out during a continuous flow. That is, the separator 4 has a small space 5 of circular disk type, provided with a hydrophobic filter 6 so as to divide the space 5 into two, an upper space 5a and a lower space 5b, wherein at the both ends of the upper space 5a, an inlet 7 for the mixture of liquids and an outlet 8 for the sample water a' are provided and at the middle of the lower space 5b, an outlet 9 for the solution b' containing oil is provided. Thus, the soluton b' which contains the extracted oil can be taken out continuously from the outlet 9, separating it through the hydrophobic filter 6 while the mixture of liquids is flowing from the inlet 7 to the outlet 8 in the upper space 5a and on the other side, the mixture of liquids is taken out continuously at the outlet 8. In FIG. 2, 10 is used to support the filter from bending. A material such as a net is generally used for the supporter in the present invention in order not to disturb the separation of the oil solution $b'$.

Since the first separator 4 is designed to separate the liquid mixture into the two components in the shortest possible time, the liquid taken out from outlet 8 not only consists of sample water $a'$, but also contains a certain amount of the extracted oil solution $b'$. Therefore, the liquid taken out from the outlet 8 is again separated precisely into the two components $a'$ and $b'$, using a second separator 11 which is much superior in separating ability than the first separator. The details of this second separator will be subsequently discussed.

In FIG. 1, 12 is an analyzer which determines the concentration of oil of the extracted oil solution $b'$ taken at the outlet 9 of the said first separator 4, (for example, it is an infra-red absorption analyzer with a condenser microphone detector, a pyreelectric detector and a semi-conductor detector, etc.) wherein the solution $b'$ is continuously introduced into a measuring cell $12_1$ fixed in the analyzer 12 and at the same time, the solvent $b$ recovered by use of a recovering device which will be explained later, is continously introduced into a reference cell $12_2$. The reason why the recovered solvent $b$ is introduced into the reference cell 12 is to prevent the occurence of error in the absorption measurement due to the decrease of the recovering ability of the adsorbent in the recovering device.

In FIG. 1, 13 is the recovering device, which is filled with an adsorbent such as, for example, active carbon, and the solution $b'$ separated by the second separator 11 and the solution $b'$ treated to measure its oil concentration in the analyzer 12 are continuously introduced into the recovering device in order to recover the solvent $b$ therefrom by the adsorption of the oil component with the adsorbent. A piping system is arranged on one side, so as to return the recovered solvent $b$ to the said extractor 3 continuously pumped by the metering pump 1, passing through the reference cell $12_2$ in the analyzer 12 and at the same time another piping system is also arranged on the other side, so as to introduce the recovered solvent $b$ directly from the recovering device 13 to the said magnetic valve 2, wherein the latter arrangement is used for the zero point check with the recovered solvent in the absorption measurement or for the purification of the piping system of the measuring apparatus.

Further, 14 is a recorder for recording the observed value obtained by the analyzer 12 and 15 is an integrator to integrate the observed value. In the present example, as the integrator 15, a mercury coulometer is used which integrates the observed value by the analyzer 12, electrochemically.

By using the apparatus exemplified above, a continuous measurement of the oil concentration in a sample can be carried out in the following manner. Using the metering pump 1, the sample water $a$ and the solvent $b$ are continuously introduced into the extractor 3, each at a definite rate and the extraction of the oil contained in the sample water $a$ is carried out continuously by use of the solvent $b$ in the extractor 3. Then the mixture is transported to the first separator 4 to separate the oil solution $b'$ (obtained by extracting the oil containing sample with the organic solvent $b$) from the mixture and the separated oil solution $b'$ is continuously introduced into the measuring cell $12_1$ in the analyzer 12 and thus, the concentration of oil is continuously measured. On the other side, the remainder portion of liquid separated from the solution $b'$ in the first separator, consisting of the sample water $a'$ and a certain amount of the solution $b'$, is sent into the second separator 11 and the two components, viz., the sample water $a'$ and the oil solution $b'$, are completely separated in this separator; the sample water $a'$ is discarded and the oil solution $b'$ is sent to the recovering device 13, all of the aforementioned process steps being carried out in a continuous manner. In the recovery device 13, the oil solution $b'$ which is introduced continuously from the measuring cell $12_1$ and the oil solution $b'$ which is introduced continuously from the second separator 11 are contacted with an adsorbent to remove the oil and recover the solvent $b$. The recovered solvent $b$ is again continuously sent to the reference cell $12_2$ in the analyzer 12 and then continuously sent to the extractor 3 through the metering pump 1 from said reference cell $12_2$.

FIG. 3 shows a detailed drawing of the second separator 11 comprising a settling tank 107 at the lower portion and a filtration tank 108 at the upper portion of the separator 109 is an inlet pipe for the mixture of liquids, which is provided in the settling tank 107 and has an opening outlet end 110 situated at the height of about one third of the height of the settling tank from the bottom. 111 is a double tube comprising an outer tube 112 and an inner tube 113 and moreover, having a passage 114 between the two tubes 112 and 113. The said outer tube 112 has a lower opening end 115 which is situated in the settling tank 107 near the bottom thereof and an upper opening 116 situated near the top of the settling tank. The inner tube 113 has a lower opening end 117 situated at a position higher than the opening end 115 but lower than the opening end 110 of the inlet pipe 109 and moreover, through the inner tube 113, the inside of the settling tank 107 and that of the filtration tank 108 are connected to each other.

The filtration tank 108 contains, in the inside thereof, a water-repulsive (hydrophobic) filter 118 which does not permit water, such as the sample water $a'$, to pass therethrough, but permits an oil such as the oil solution $b'$ (consisting of e.g. carbon tetrachloride and an oil) to pass through it. Furthermore, at a position upper than the filter 118, inlet holes 119, connected to the upper portion of said inner tube 113, are provided and at a position higher than the inlet holes 119, there is further provided an exhaust outlet 120 for exhausting the separated sample water $a'$ as a waste water. 121 is an opening hole provided at a position lower than the filter 118 in the filtration tank 108 for taking out the separated oil solution $b'$ and 122 is an outlet for the separated oil solution $b'$, which outlet is connected to the opening hole 121 and released to the atmospheric air. The oil solution $b'$ (e.g. a carbon tetrachloride solution of oil extracted from the sample water through filter 118), is taken out from the outlet 122. The outlet 122 is provided at a proper height so that it is higher than that of the filter 118 so as to permit the filter 118 to remain dipped within the carbon tetrachloride solution introduced into the filtration tank 108. Furthermore, the filtration tank 108 is designed so as to be able to separate it into two parts, that is, an upper part 108' over the filter 118 and a lower part 108'' under the filter, wherein the filter can be exchanged after removing the upper part 108'. 123 in FIG. 3 is an outlet for the mixture of liquids, 124 is an exhaust outlet for purging with air and 125 is an exhaust valve for dusts.

In accordance with the operation of the separator 11, as shown in FIG. 3, a mixture of oil-containing carbon tetrachloride and water having suspended foreign substances, is introduced into the settling tank 107 through the lower opening outlet 110 from the inlet 123. Then, the carbon tetrachloride solution, which is heavier than water, comes down into the bottom side of the settling tank and the water fills up the upper portion of the tank. At the same time, the filtration tank is also filled up with said liquids through the lower opening 117 of the inner tube 113. In this case, the height of the interface between the carbon tetrachloride solution and the water in the settling tank is different depending upon the mixing ratio of the two liquids. That is, if the volume of the carbon tetrachloride solution is larger than that of the sample water in the mixture, for example, the interfacial level becomes higher than the lower opening end 117 of the inner tube 113 and accordingly, only the carbon tetrachloride solution is sent from the lower opening 117 into the filtration tank 108, forced by the head difference between the mixture inlet 123 and the water outlet 120. And in this case, the interfacial level between the two liquids in the inside of the outer tube 112 is, of course, equal in height to that of the interfacial level in the settling tank itself, since the outer tube 112 has two openings 115 and 116 at the lowest end and top, respectively. As the feeding of the mixture into the settling tank 107 progresses, the sample water gradually accumulates in the tank, decreasing the interfacial level height up to near the position of the lower opening end 117 until it becomes possible to let the water component go to the filtration tank through the lower opening 117. Thus, the interfacial level fluctuates near the opening end 117, passing the two liquid components through the opening 117. In this process, it can be pointed out that the entrances of the two liquid components $a'$ and $b'$ to lead them to the lower opening 117 of the inner tube 113 are limited to only the lower opening 115 and the upper opening 116, since there exists the outer tube 112 surrounding the opening end 117. That is, the carbon tetrachloride solution $b'$ flows from the lower opening 110 to the opening 115 of the outer tube 112 at first, separating the dusts designated 126, 127 and 128 from the carbon tetrachloride layer in such a way that it permits the dust 126 which is lighter than the sample water, to float up, while permitting the dust 127, which is heavier than the carbon tetrachloride, to sink down and permitting the dust 128 having an intermediate density to float around the interface. Then, the carbon tetrachloride solution reaches the lower opening 117 of the inner tube. On the other side, the sample water $a'$, at first, flows from the lower opening end 110 to the upper opening 116 of the outer tube 112, separating those dusts 126, 127 and 128 in the same way as in the previous case mentioned above, until the sample water $a'$ reaches the opening 117 of the inner tube. Thus, as a result of the rather long passage of the water component $a'$, mentioned above, the residual portion of the carbon tetrachloride solution, which is dispersed as fine particles in the aqueous phase, can be completely eliminated as large particles.

As explained above, in the settling tank 107, clarificaton occurs automatically and the sample water and the carbon tetrachloride solution, free from the dusts 126, 127 and 128 are sent to the filtration tower 108. Further, although it is true that the floating dust 128 has a specific gravity situated between that of water and that of carbon tetrachloride, it neves does enter into the opening 117, as a result of the disturbance due to the existence of the outer tube 112. Thus, in the filtration tank 108, the carbon tetrachloride solution, free from dusts, rapidly passes through the filter 118 and is taken out from the outlet 122. Since the sample water $a'$ does not pass through the filter, it is exhausted from the outlet 120. Furthermore, since the outlet 122 (opened to the atmosphere as already stated) is situated higher than the filter 118, the filter is always in a dipped state in the carbon tetrachloride solution and accordingly, maintains an ability to filter only the carbon tetrachloride solution quickly for a long period without losing this ability by having its fine pores choked with the water.

By using the second separator 11 of the present invention, it is possible to separate the carbon teterachloride solution effectively and precisely from the sample water for a long period, since only the water component and the oil solution, rendered completely free from various dusts by the treatment in the settling tank 107, are sent to the filtration tank 108. Accordingly, the fine holes of the filter are never choked with dusts and, of course, it is possible to carry out the separation continuously, introducing the mixture of water and carbon tetrachloride containing oil into the settling tank 107 in a continuous manner.

As stated above, the apparatus of the present invention makes it possible to carry out the measurement of the oil concentration continuously for a long period of time, wherein the oil solution of an organic solvent prepared in the extractor is rapidly separated from the remainder of the sample water and a certain amount of the oil contaminated solution in the first separator is quickly sent to the measuring cell of the analyzer in a continuous manner. That is, the purpose of the separation of the oil solution in the first separator is not a complete separation of the oil solution from the sample water, but is a quick sampling for analysis and the complete separation is carried out in the second separator by feeding said remainder portion into it.

Thus, it is possible to get an analytical response very quickly in the apparatus of the present invention. Furthermore, it is possible to carry out a very accurate measurement of the oil concentration by using the apparatus of the present invention, even though the recovering ability of the adsorbent in the recovering device is decreased, since this is compensated for by introducing the recovered solvent into the reference cell.

Finally, the apparatus of the present invention is economical and could not in any way be considered a public nuisance, since the separation of the oil solution from the aqueous component is completely carried out using separators in two steps and the oil solution is repeatedly used after every recovery, without exhausting it to the outside.

What is claimed is:

1. An apparatus for the continuous measurement of the concentration of oil in a water sample, comprising a supplying device which supplies an oil-containing water sample and a supplying device which supplies a solvent for extracting the oil in the sample, each of said water sample and solvent being supplied in a controlled and continuous amount, an extractor connected to said supplying devices having an agitator therein, which extractor receives said oil-containing water sample and solvent and serves to extract the oil component in the water sample with the solvent; a first separator connected to said extractor and which receives the mixture of oil-containing solvent and extracted water sample from the extractor and serves to quickly but incompletely separate the oil-containing solvent and extracted water sample, said first separator containing an inlet to receive the mixture of oil-containing solvent and extracted sample from the extractor, a hydrophobic filter to separate the oil-containing solvent from the extracted water sample, one outlet for removing the oil-containing solvent and another outlet for removing a mixture of the extracted water sample and oil-containing solvent which have not been separated; an infra-red analyzer containing two cells for measuring the concentration of oil, one cell being connected directly to the outlet of the first separator for removing the separated oil-containing solvent therefrom and which cell receives said oil-containing solvent and measures the concentration of oil in said oil-containing solvent and a second reference cell; a second separator connected to said first separator for receiving the sample water and the oil-containing solvent not separated in the first separator and which serves to separate the oil-containing solvent from the water sample, said second separator containing an outlet to remove and discard the separated water sample, and an outlet to remove the separated oil-containing solvent; a solvent recovery device connected to both the second separator and the first cell in the infra-red analyzer and which receives the oil-containing solvents from both the second separator and first cell, and which contains an adsorbent to remove the oil from the oil-containing solvent so as to recover the solvent with the oil removed therefrom.

2. An apparatus according to claim 1, wherein the solvent recovery device contains at least one outlet which is connected to the reference cell in the infrarred analyzer to prevent the occurrence of error in the absorption measurement due to the decrease of the recovery ability of the adsorbent in the recovering device.

3. An apparatus according to claim 1 having an integrator for integrating the observed intensity of the infra-red absorption continuously obtained by the infrared analyzer.

* * * * *